United States Patent [19]

Engelbach et al.

[11] 4,392,984
[45] Jul. 12, 1983

[54] OLEFIN OLIGOMERIZATION CATALYSTS AND A PROCESS FOR THEIR PREPARATION

[75] Inventors: Heinz Engelbach; Werner Steigleiter, both of Limburgerhof; Helmut Glietenberg, Ludwigshafen, all of Fed. Rep. of Germany

[73] Assignee: BASF Aktiengesellschaft, Ludwigshafen, Fed. Rep. of Germany

[21] Appl. No.: 247,624

[22] Filed: Mar. 25, 1981

[30] Foreign Application Priority Data

Apr. 18, 1980 [DE] Fed. Rep. of Germany ....... 3014950

[51] Int. Cl.$^3$ .................. B01J 21/02; B01J 21/06; B01J 23/18; B01J 27/18
[52] U.S. Cl. .................................. 252/432; 252/435; 585/514
[58] Field of Search ................ 252/432, 435; 585/514

[56] References Cited

U.S. PATENT DOCUMENTS 2,620,364 12/1952 Krug ............................. 252/432 X
3,213,036 10/1965 Morrell ............................. 252/435
3,244,767 4/1966 Nixon .
3,426,089 2/1969 Rosset .
3,689,589 9/1972 Reusser ............................. 252/437 X

FOREIGN PATENT DOCUMENTS 1374756 8/1964 France .
50-30046 9/1975 Japan ............................. 585/514

OTHER PUBLICATIONS

E. G. Hancock, "Propylene & Its Industrial Derivatives", Ernest Benn Ltd., (1973).

Primary Examiner—W. J. Shine
Attorney, Agent, or Firm—John H. Shurtleff

[57] ABSTRACT

Catalysts, for olefin oligomerization, whose active material has the empirical formula I $$APO_4 \cdot [P_2O_5 \cdot (H_2O)_n]_a \cdot (XY)_b \qquad I$$

where A is boron, antimony, bismuth, aluminum and/or 3 equivalents of titanium, X is $NH_4^\oplus$ and/or an alkali metal cation and/or one equivalent of an alkaline earth metal cation, Y is one equivalent of an anion, a is 0.02–0.2, b is 0–0.05 and n is 1–3, and a process for the preparation of these catalysts.

4 Claims, No Drawings

OLEFIN OLIGOMERIZATION CATALYSTS AND A PROCESS FOR THEIR PREPARATION

The present invention relates to novel catalysts based on boron phosphate, antimony phosphate, bismuth phosphate, aluminum phosphate or titanium phosphate or on mixed phosphates of these elements, and to a process for olefin oligomerization, using these catalysts.

The oligomerization of propene under superatmospheric pressure and at elevated temperatures, over supported catalysts containing phosphoric acid, to form trimers, tetramers and higher oligomers, is well-known, for example from the monograph by E. G. Hancock "Propylene and its Industrial Derivatives", published by Ernest Benn, London, 1973, page 138 et seq. As is also well-known, basically the same method can be employed to oligomerize, for example, the butenes.

Both the prototype of the catalysts used for this purpose, namely $SiO_2$ impregnated with phosphoric acid, and numerous variants employing additional components, such as sulfur compounds and fluorine compounds (U.S. Pat. Nos. 3,244,767 and 3,426,089), are unsatisfactory as regards catalyst life and as regards selectivity in respect of the oligomers principally desired, namely propene trimers and butene dimers. At high olefin conversions, in particular, the selectivity is unsatisfactory, ie. mixtures of oligomers with various degrees of oligomerization are obtained, containing high proportions of undesired oligomers.

The $H_3PO_4/SiO_2$ supported catalysts of French Pat. No. 1,374,756, in which part of the $SiO_2$ is replaced by other oxides, including boron trioxide, also do not conform to requirements. With these catalysts, where the molar ratio of $P_2O_5$ to $B_2O_3$ is from about 9:1 to 40:1, it is possible to achieve propene conversions of about 90%, as our own experiments have shown, but the desired product, namely trimeric propene, is obtained in a selectivity, ie. a yield based on propene conversion, of only about 75%. Furthermore, the conversion, using these catalysts, drops to about 70–75% after about one month's operation.

It is an object of the present invention to provide catalysts for olefin oligomerization, with which constant high conversions can be achieved over long periods. Specifically, it is an object of the invention to provide such catalysts for oligomerizing propene and butenes, with high selectivities in respect of propene trimers and butene dimers.

We have found that this object is achieved and that mixed compounds which have the empirical formula

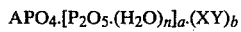

$$APO_4 \cdot [P_2O_5 \cdot (H_2O)_n]_a \cdot (XY)_b \qquad I$$

where A is boron, antimony, bismuth, aluminum and/or 3 equivalents of titanium, X is $NH_4^\oplus$ and/or an alkali metal cation and/or one equivalent of an alkaline earth metal cation, Y is one equivalent of an anion, a is 0.02–0.2, b is 0–0.05 and n is 1–3, are outstandingly suitable catalysts for olefin oligomerization.

Amongst these catalysts, those wherein A is boron or the proportion of boron in A is not less than 80 mole % are particularly preferred. The invention will therefore be explained in more detail in relation to the catalysts based on boron phosphate. The general sense of the explanations applies correspondingly to the other phosphates or mixed phosphates falling within the definition.

In the simplest case, these catalysts comprise a mixed compound of $BPO_4$ with orthophosphoric acid (n=3) or with an anhydro-phosphoric acid (n=1 to n=3 as the limiting case). It is characteristic of these mixed compounds that they substantially, ie. up to not less than 95% of the theoretically possible value, exhibit the structure of $BPO_4$, as can be established by means of the X-ray diffraction diagram.

These catalysts may be prepared by thoroughly mixing aqueous or pure phosphoric acid and boric acid, keeping the mixture at 80°–120° C. under reflux for 2–30 hours, whilst stirring, and then continuing heating at about 80°–120° C., whilst substantially removing the water which is not bonded chemically, until the material has become viscous. The product is then dried and dehydrated at 110°–500° C. until the water content corresponds to the desired value of n. Said water content can be simply determined gravimetrically in the usual manner. Thereafter, the mass is pulverized, kneaded with a small amount of water to form a paste, and molded to the desired shape, for example spheres, tablets, extrudates or rings. The extrudates are in general 2–40 mm long, with a diameter of 1–20 mm. These dimensions apply correspondingly to the other shapes. After molding, the product is again dried and dehydrated. In the interest of the mechanical strength of the catalyst particles it is advisable to dry the material gently, for example by heating the particles first for 2–30 hours at 80°–120° C. and then for 2–40 hours at 120°–500° C.

It is also possible to carry out the mixing of the boric acid and phosphoric acid, accompanied by formation of boron phosphate, at a lower temperature, for example at room temperature, the time allowed being correspondingly longer. Furthermore, molding can also be carried out with the material obtained after the first heating, but in that case boron phosphate formation is in most cases not quite complete. If the material is heated to a very high temperature, $P_2O_5$ may sublime. The resulting losses can however be made good by adding corresponding amounts of phosphoric acid.

Of course it is also possible to employ, instead of phosphoric acid, the anhydride-acids, eg. metaphosphoric acid, pyrophosphoric acid and polyphosphoric acids, and to employ boron trioxide instead of boric acid. The efficiency of the catalyst can be further improved by additives corresponding to $(XY)_b$ in the formula. In such additives, X is the ammonium cation, an alkali metal cation or one cation equivalent of an alkaline earth metal. Preferred metals are Na, K and Ca. These catalysts are prepared in a similar manner to the additive-free catalysts, but in the presence of corresponding amounts of salts XY, where Y is the equivalent anion. According to our observations hitherto, the nature of the anion is immaterial, so that, for example, the nitrates, sulfates or chlorides may be employed. However, the borates and phosphates, or salts, for example carbonates or formates, which during preparation of the catalysts are converted to the borates or phosphates, are preferred. If Y is borate or phosphate, it must be included, as $B_2O_3$ or $P_2O_5$, in calculating the total $B_2O_3$ or $P_2O_5$ in the empirical formula I. In that case, Y would thus be the anionic oxygen bonded to B or P.

The chemical structure of the catalysts is not known in detail, but the catalysts prove active whenever they correspond to the empirical formula I and when, according to the X-ray diffraction diagram, the boron is present to the extent of at least 95% as boron phosphate.

Preferably, the novel catalysts are used as unsupported catalysts. However, it is also possible to apply the active material to inert carriers, eg. $SiO_2$, $Al_2O_3$ or steatite, by conventional techniques, in amounts such that the carrier constitutes from about 30 to 95% by weight of the complete supported catalyst.

Olefin oligomerization, using the novel catalysts, can be carried out batchwise or, preferably, continuously, in a gaseous, liquid or fluid phase, by conventional techniques and under conventional conditions, ie. at 50°–300° C., preferably 100°–200° C., and 10–200 bar, preferably 80–150 bar, using, as the feed, either the pure olefin or, preferably, a mixture containing not less than 10% by weight of olefin, the remainder being an inert gas, preferably the corresponding paraffin.

For continuous oligomerization, which is the preferred method, the catalyst is advantageously arranged as a fixed loosely packed bed and the olefin throughput is controlled to give a conversion of 0.25–6 liters of liquid olefin per liter of catalyst volume per hour. Suitable olefins are, in principle, all olefinically unsaturated polymerizable compounds, or particularly $C_2$–$C_6$-α-alkenes. Instances of particular practical importance are the trimerization of propene and the dimerization and co-dimerization of but-1-ene, but-2-ene and isobutene, which respectively give a mixture of nonene isomers and of octene isomers. The co-dimerization of butenes with propene to give heptenes can also be carried out successfully. These higher olefins can then be converted respectively to decanols, nonanols and octanols by hydroformylation and hydrogenation, and these alcohols can in turn be used to prepare plasticizers and detergents.

EXAMPLES A–D

Preparation of catalysts of type $BPO_4.[P_2O_5.(H_2O)_n]_a$

To prepare catalyst A, 1,000 g of pure orthophosphoric acid, 176.5 g of water and 560 g of boric acid were refluxed, with stirring, for 15 hours at 112° C., after which sufficient water was distilled off to leave a viscous pasty material. The latter was dried for 15 hours at 110° C. and 24 hours at 230° C., and pulverized, the powder was kneaded with 465 g of water to give a viscous paste, and the latter was molded to give extrudates of 4 mm diameter and 4 mm length. These extrudates were then dried for 15 hours at 110° C. and 24 hours at 230° C.

Catalysts B and C and Comparative Catalyst D were prepared similarly. The characteristics of these catalysts are shown in Table 1.

EXAMPLES E–N

Preparation of catalysts of type $BPO_4.[P_2O_5.(H_2O)_n]_a.(XY)_b$

These catalysts were prepared in the same way as Catalysts A–D, except that a proportion of the phosphoric acid was replaced by ammonium dihydrogen phosphate, or by an alkali metal dihydrogen phosphate or by an alkaline earth metal hydrogen phosphate. The characteristics of these catalysts are also shown in Table 1.

EXAMPLES O–R

Preparation of catalysts of type $APO_4.[P_2O_5.(H_2O)_n]_a$

These catalysts, which differ from Catalysts A–N in that they contain a different element A, were prepared similarly to Catalysts A–N, but employing oxides of Sb, Bi, Ti and Al. The characteristics of these catalysts are also shown in Table 1.

TABLE 1

Catalysts $BPO_4.[P_2O_5.(H_2O)_n]_a.(XO-)_b$

| Catalyst | A | a | n | X | b | Boron phosphate, according to X-ray diffraction diagram % |
|---|---|---|---|---|---|---|
| A | Boron | 0.045 | 1.8 | — | — | in all |
| B | " | 0.063 | 1.8 | — | — | cases |
| C | " | 0.150 | 1.8 | — | — | ≧95% |
| D, for comparison | " | 0.250 | 1.8 | — | — | |
| E | " | 0.072 | 1.8 | $NH_4$ | 0.0071 | |
| F | " | 0.076 | 1.8 | $NH_4$ | 0.0125 | |
| G | " | 0.072 | 1.8 | $NH_4$ | 0.0214 | |
| H | " | 0.072 | 1.8 | $NH_4$ | 0.0285 | |
| I | " | 0.063 | 1.8 | K | 0.00625 | |
| K | " | 0.063 | 1.8 | K | 0.0125 | |
| L | " | 0.063 | 1.8 | Na | 0.0125 | |
| M | " | 0.063 | 1.8 | Rb | 0.0125 | |
| N | " | 0.063 | 1.8 | Ca | 0.00625 | |
| O | Sb | 0.025 | 1.8 | — | — | — |
| P | Bi | 0.063 | 1.8 | — | — | — |
| Q | Ti | 0.050 | 1.8 | — | — | — |
| R | Al | 0.063 | 1.8 | — | — | — |

EXAMPLES 1–18

Trimerization of propene 300 ml of catalysts A–Q were loosely packed into a cylindrical test reactor of 3 cm internal diameter and 2 m length. A mixture of 50% by weight of propane and 50% by weight of propene was subjected to propene oligomerization, aimed at trimerization, at a throughput of 0.5 liter of liquid propene per liter of catalyst volume per hour, the other reaction conditions being shown in Table 2; the values given relate to steady-state operation. The temperature was in each case that of the cooling medium ($^R$Marlotherm), which surrounded the reactor and was, in turn, kept at constant temperature by water cooling.

The results, determined by the conventional methods of analysis, such as boiling analysis, gas chromatography and determination of the hydrogenation iodine number, are also shown in Table 2. In all cases, the materials formed additionally to the nonenes were principally the dodecenes, with small amounts of higher oligomers. The proportion of hexenes and other by-products was negligible.

In no case was a decline in catalyst activity, in respect of conversion or selectivity, noted over the duration of the experiment, namely from 5 to 30 days.

TABLE 2

Trimerization of propene to nonenes

| Example | Catalyst | Temp. °C. | Pressure bar | Propene conversion % | Yield of nonene based on conversion % | Yield of nonene absolute % |
|---|---|---|---|---|---|---|
| 1 | A | 150 | 100 | 91 | 71 | 65 |
| 2 | B | 150 | 100 | 88 | 77 | 68 |
| 3 | C | 126 | 100 | 86 | 73 | 63 |
| 4++ | D++ | 130 | 100 | 92 | 54 | 50 |
| 5 | B | 140 | 150 | 88 | 76 | 67 |
| 6 | B | 140 | 100 | 89 | 74 | 66 |
| 7 | E | 140 | 100 | 84 | 79 | 66 |
| 8 | F | 150 | 100 | 86 | 77 | 66 |

TABLE 2-continued

Trimerization of propene to nonenes

| Example | Catalyst | Temp. °C. | Pressure bar | Propene conversion % | Yield of nonene based on conversion % | absolute % |
|---|---|---|---|---|---|---|
| 9 | G | 175 | 100 | 87 | 90 | 78 |
| 10 | H | 195 | 100 | 80 | 86 | 69 |
| 11 | I | 150 | 100 | 84 | 74 | 62 |
| 12 | K | 175 | 100 | 84 | 87 | 73 |
| 13 | L | 150 | 100 | 84 | 81 | 68 |
| 14 | M | 140 | 100 | 88 | 74 | 65 |
| 15 | N | 150 | 100 | 85 | 78 | 66 |
| 16 | O | 140 | 100 | 89 | 72 | 64 |
| 17 | P | 190 | 100 | 42 | 83 | 35 |
| 18 | Q | 135 | 100 | 96 | 73 | 70 |

$^+$ = selectivity
$^{++}$ = for comparison

EXAMPLE 19

Dimerization of butenes 24.3 g of catalyst G, which had a particle size of 1–1.5 mm, were loosely packed into a test reactor of 8 mm internal diameter and 90 cm height.

A butene-containing hydrocarbon fraction of the following composition

| | |
|---|---|
| but-1-ene | 12.9 % by volume |
| cis-but-2-ene | 23.0 % by volume |
| trans-but-2-ene | 43.5 % by volume |
| isobutene | 0.9 % by volume |
| buta-1,3-diene | 0.03 % by volume |
| propene | 0.73 % by volume |
| butane | 15.7 % by volume |
| isobutane | 3.1 % by volume | was dimerized at 225° C. and 90 bar, with an hourly throughput of 1.75 liters of liquid butenes per liter of catalyst volume.

The butene conversion was 82%, the selectivity in respect of dimers was 89%, and the absolute yield was accordingly 73%. These results remained constant over a period of observation of 10 days.

EXAMPLE 20

Dimerization of butenes

The hydrocarbon mixture described in Example 19 was dimerized by a method similar to that described there, but using catalyst R and a throughput of 0.28 liter of liquid butenes per liter of catalyst volume.

The butene conversion was 73%, the selectivity in respect of the dimers was 74% and the absolute yield of dimers was accordingly 54%.

EXAMPLE 21

The hydrocarbon mixture mentioned in Example 19 was dimerized by a method similar to that described there, but using catalyst S $$BPO_4[P_2O_5.(H_2O)_{1.8}]_{0.072}.[NH_4(SO_4)_{0.5}]_{0.0143}$$

which was prepared like catalysts E–N, the throughput being 0.5 liter of liquid butenes per liter of catalyst volume and the temperature being 180° C. The butene conversion was 81% and the selectivity in respect of the dimers was 88%, so that the dimers were obtained in an absolute yield of 71%.

We claim:
1. A catalyst for olefin oligomerization, whose active material has the empirical formula

$$APO_4.[P_2O_5.(H_2O)_n]_a.(XY)_b \qquad \text{I}$$

where A is boron, antimony, bismuth or 3 equivalents of titanium or mixtures thereof, X is $NH_4^\oplus$ or an alkali metal cation and/or one equivalent of an alkaline earth metal cation, or mixtures thereof Y is one equivalent of an anion, a is 0.02–0.2, b is 0–0.05 and n is 1–3.

2. A catalyst as claimed in claim 1, wherein A is boron.

3. A process for the preparation of the catalyst as claimed in claim 1, wherein aqueous or pure phosphoric acid or an anhydrophosphoric acid is thoroughly mixed with an oxide of element A, with or without addition of a salt XY, in the ratios corresponding to the indices a and b, the mixture is heated for a lengthy period, the excess water is distilled off until a viscous or solid material is obtained, the latter is brought to the desired catalyst shape and the catalyst particles are dried at an elevated temperature until the content of chemically bonded water corresponds to the desired value of n.

4. A process as claimed in claim 3, wherein the viscous or solid material first obtained is dried at an elevated temperature, the dry material is pulverized, the powder is worked into a paste with water, the paste is then molded and the catalyst particles are dried until the content of chemically bonded water corresponds to the desired value of n.

* * * * *